(12) United States Patent
Kosugi

(10) Patent No.: US 12,390,089 B2
(45) Date of Patent: *Aug. 19, 2025

(54) PROCESSOR FOR ENDOSCOPE, ENDOSCOPE SYSTEM, INFORMATION PROCESSING APPARATUS, NON-TRANSITORY COMPUTER-READABLE STORAGE MEDIUM, AND INFORMATION PROCESSING METHOD USING LEARNING MODELS

(71) Applicant: HOYA CORPORATION, Tokyo (JP)

(72) Inventor: Kenta Kosugi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 823 days.

This patent is subject to a terminal disclaimer.

(21) Appl. No.: 17/634,389

(22) PCT Filed: Aug. 16, 2019

(86) PCT No.: PCT/JP2019/032134
§ 371 (c)(1),
(2) Date: Feb. 10, 2022

(87) PCT Pub. No.: WO2021/033216
PCT Pub. Date: Feb. 25, 2021

(65) Prior Publication Data
US 2022/0322915 A1    Oct. 13, 2022

(51) Int. Cl.
*A61B 1/00* (2006.01)
(52) U.S. Cl.
CPC ...... *A61B 1/00057* (2013.01); *A61B 1/00006* (2013.01); *A61B 1/000096* (2022.02); *A61B 1/00055* (2013.01)
(58) Field of Classification Search
CPC ............ A61B 1/00057; A61B 1/00006; A61B 1/000096; A61B 1/00059
See application file for complete search history.

(56) References Cited

U.S. PATENT DOCUMENTS 8,357,094 B2 * 1/2013 Mo .......................... A61B 8/00
600/407
9,588,046 B2    3/2017 Ishihara et al.
(Continued)

FOREIGN PATENT DOCUMENTS

CN    109447973    3/2019
JP    2013-56001    3/2013
(Continued)

OTHER PUBLICATIONS

International Search Report issued in International Patent Application No. PCT/JP2019/032134, dated Nov. 5, 2019, along with an English translation thereof.

(Continued)

*Primary Examiner* — Benjamin O Dulaney
(74) *Attorney, Agent, or Firm* — Greenblum & Bernstein, P.L.C.

(57) ABSTRACT

A processor for an endoscope according to an aspect is characterized by including: a controller executing program code to perform: acquiring, by the controller, an endoscopic image captured using first system information; calculating, by the controller, parameter on the basis of the endoscopic image acquired by the controller; discriminating a part of a subject using a first learning model that outputs a discrimination result of discriminating the part of the subject in a case in which the calculated parameter is input; outputting second system information using a second learning model that outputs the second system information in a case in which the parameter and the discriminated part of the subject are input; and determining, by the controller, a difference between the second system information output by the second learning model and the first system information.

16 Claims, 16 Drawing Sheets

(56) References Cited

U.S. PATENT DOCUMENTS

| | | |
|---|---|---|
| 2014/0184769 A1 | 7/2014 | Ishihara et al. |
| 2018/0144466 A1 | 5/2018 | Hsieh et al. |
| 2018/0153384 A1 | 6/2018 | Ikemoto et al. |
| 2018/0325354 A1* | 11/2018 | Saito .................. G06T 7/35 |
| 2019/0034800 A1 | 1/2019 | Shiratani |
| 2019/0122378 A1* | 4/2019 | Aswin .................. G06T 7/20 |
| 2019/0303181 A1* | 10/2019 | Mori .................. H04N 1/00506 |
| 2019/0311476 A1 | 10/2019 | Hayami et al. |
| 2019/0324252 A1* | 10/2019 | Mak .................. G02B 21/06 |
| 2019/0374094 A1 | 12/2019 | Yamamoto |
| 2020/0022610 A1* | 1/2020 | Zenge .................. G16H 30/00 |
| 2020/0089983 A1* | 3/2020 | Manickam ............ G06V 10/82 |
| 2020/0402204 A1* | 12/2020 | Huang .................. G06T 11/003 |
| 2021/0004959 A1 | 1/2021 | Fu et al. |
| 2021/0007760 A1* | 1/2021 | Reisin .................. G16H 40/63 |
| 2021/0149182 A1* | 5/2021 | Hayami ............ G02B 23/2484 |
| 2021/0342592 A1* | 11/2021 | Oosake ............ A61B 1/00045 |
| 2021/0398259 A1* | 12/2021 | Yamazoe .................. G06T 5/70 |
| 2022/0233171 A1* | 7/2022 | Johnson .................. A61B 8/585 |
| 2022/0237787 A1* | 7/2022 | Ewald .................. G06V 10/82 |
| 2022/0277835 A1* | 9/2022 | Senegas .............. A61B 6/5247 |
| 2022/0392068 A1 | 12/2022 | Fu et al. |

FOREIGN PATENT DOCUMENTS

| | | |
|---|---|---|
| JP | 2014-36738 | 2/2014 |
| JP | 2016-158682 | 9/2016 |
| WO | 2016/208016 | 12/2016 |
| WO | 2017/126425 | 7/2017 |
| WO | 2018/105063 | 6/2018 |
| WO | 2018/159083 | 9/2018 |

OTHER PUBLICATIONS

Mar. 27, 2023 Extended European Search Report in corresponding European Application No. 19941927.6.

* cited by examiner

FIG. 4

| MANAGEMENT ID | IMAGE SETTING | | | | LAMP APERTURE | VOLTAGE/ CURRENT |
|---|---|---|---|---|---|---|
| | RED | BLUE | BRIGHTNESS | ENHANCEMENT | | |
| 001 | 2 | 1 | level3 | Med | ****** | ****** |

| ITEM ID | CATEGORY | ITEM | THRESHOLD VALUE |
|---|---|---|---|
| 001 | IMAGE SETTING | RED | -5～+5 |
| 002 | | BLUE | -5～+5 |
| 003 | | BRIGHTNESS | level1～level5 |
| 004 | | ENHANCEMENT | Off, Low, Med, High |
| 005 | LIGHT SOURCE DEVICE | LAMP APERTURE AMOUNT | ****** |
| 006 | | VOLTAGE APPLIED TO THE LAMP | ****** |

274

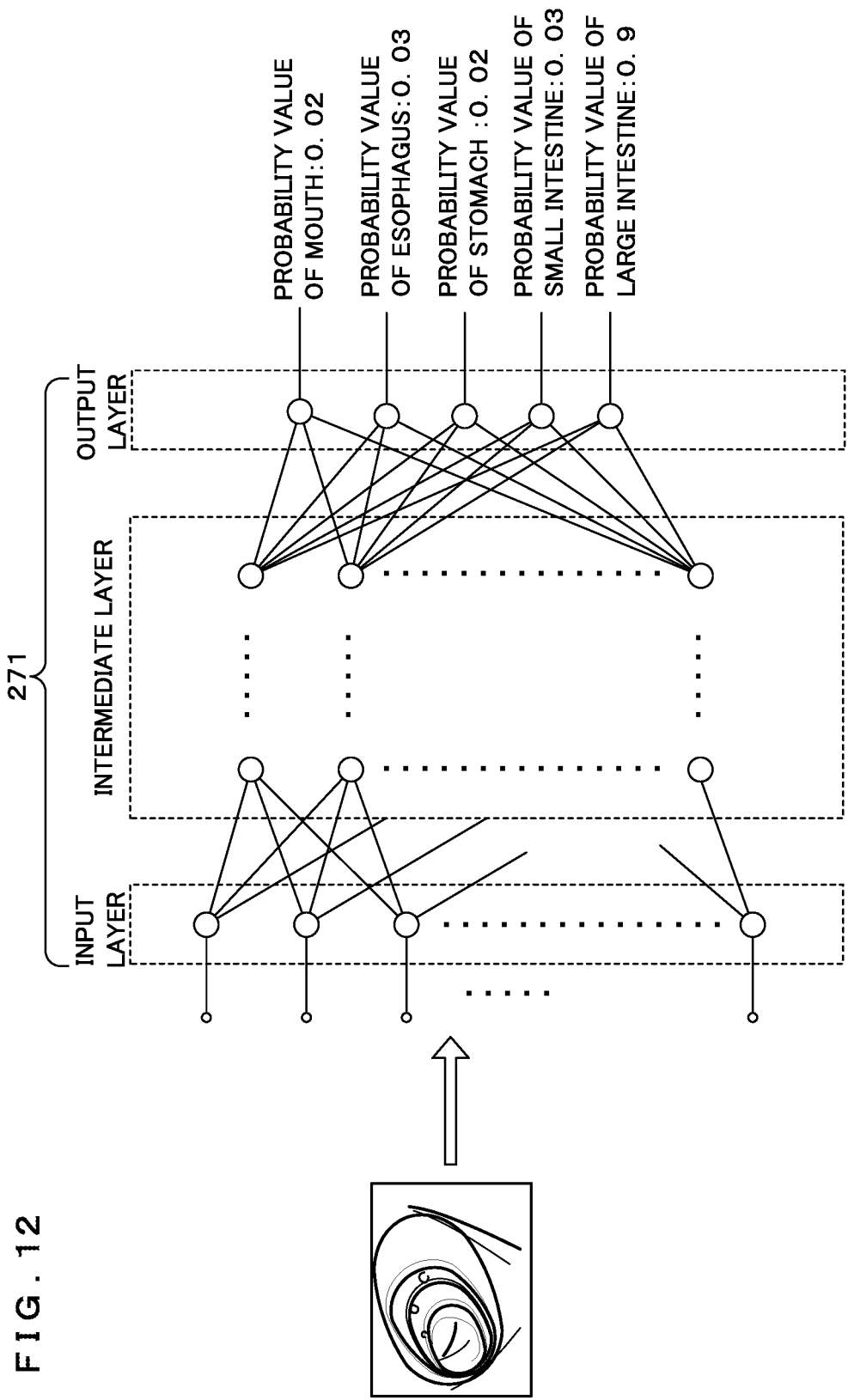

PROCESSOR FOR ENDOSCOPE, ENDOSCOPE SYSTEM, INFORMATION PROCESSING APPARATUS, NON-TRANSITORY COMPUTER-READABLE STORAGE MEDIUM, AND INFORMATION PROCESSING METHOD USING LEARNING MODELS

CROSS-REFERENCE TO RELATED APPLICATIONS

This application is the national phase under 35 U.S.C. § 371 of International Patent Application No. PCT/JP2019/032134 which has an International filing date of Aug. 16, 2019 and designated the United States of America.

FIELD

The present disclosure relates to a processor for an endoscope, an endoscope system, an information processing device, a program, and an information processing method.

BACKGROUND

In recent years, there have been various image processing techniques for improving the accuracy of detection in endoscopy. An image processing device that prevents the positional deviation between a mark indicating a site of lesion which is attached to an endoscopic image and the endoscopic image (see Japanese Patent Laid-Open Publication No. 2016-158682, for example).

However, in the invention disclosed in the Japanese Patent Laid-Open Publication No. 2016-158682, when a system abnormality that affects image quality occurs, there is a concern that it will be difficult to correctly specify the cause of the abnormality (for example, image settings, an optical system, a light source, an electric circuit, or the like).

SUMMARY

A processor for an endoscope according to an aspect is characterized by including: a controller executing program code to perform: acquiring, by the controller, an endoscopic image captured using first system information; calculating, by the controller, parameter on the basis of the endoscopic image acquired by the controller; discriminating a part of a subject using a first learning model that outputs a discrimination result of discriminating the part of the subject in a case in which the calculated parameter is input; outputting second system information using a second learning model that outputs the second system information in a case in which the parameter and the discriminated part of the subject are input; and determining, by the controller, a difference between the second system information output by the second learning model and the first system information.

The above and further objects and features will more fully be apparent from the following detailed description with accompanying drawings.

BRIEF DESCRIPTION OF THE DRAWINGS

FIG. 4 is an explanatory diagram illustrating an example of a record layout of a system information DB.

FIG. 5 is an explanatory diagram illustrating an example of a record layout of a threshold value DB.

FIG. 12 is an explanatory diagram describing a part discrimination model according to Embodiment 2.

DETAILED DESCRIPTION

Hereinafter, the disclosure will be described in detail with reference to the drawings illustrating embodiments of the disclosure.

Embodiment 1

Figure 1:
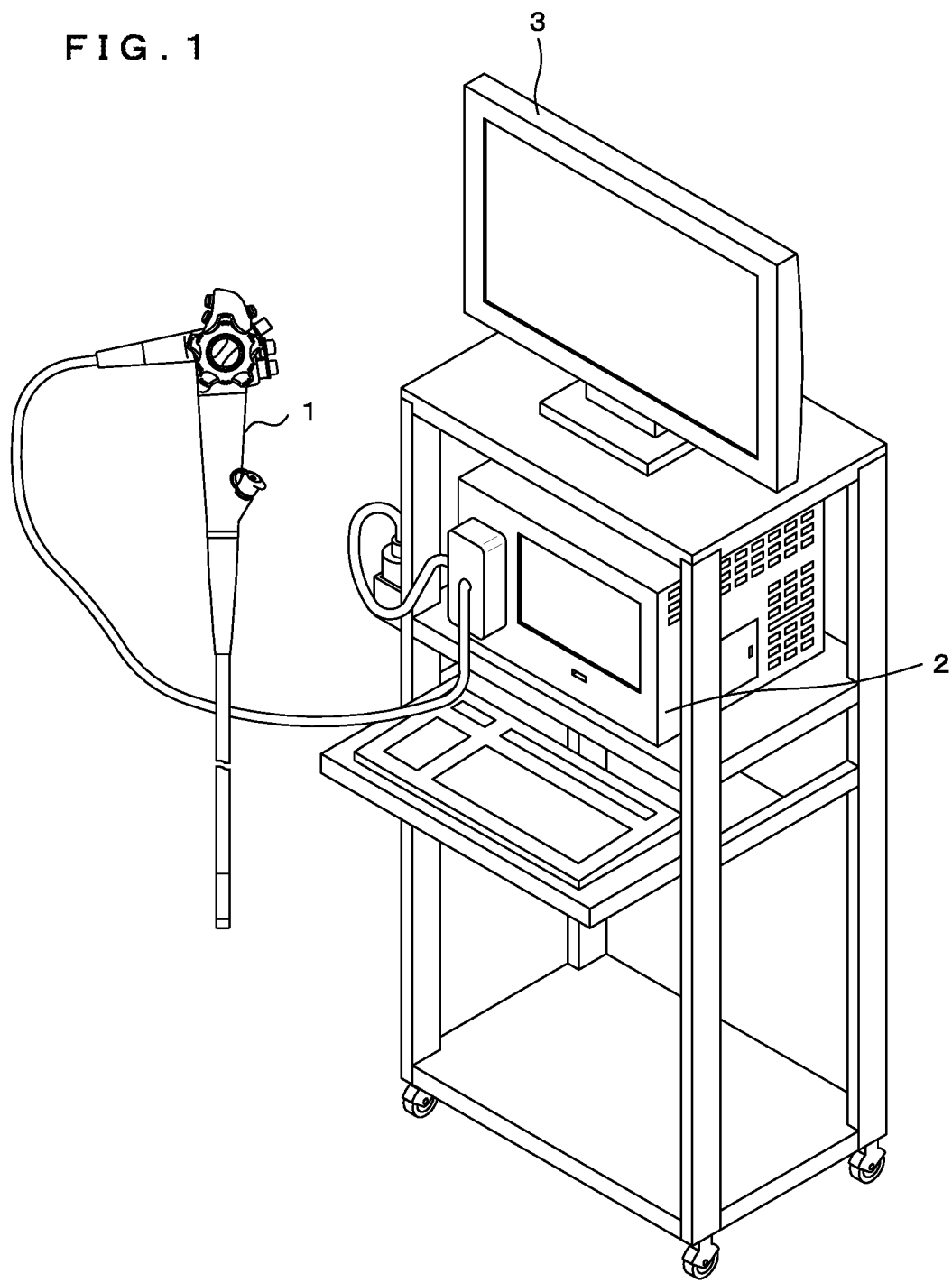
FIG. 1 is a schematic diagram illustrating an example of the configuration of an endoscope system.

Embodiment 1 relates to an aspect in which a system abnormality is monitored using artificial intelligence (AI). FIG. 1 is a schematic diagram illustrating an example of the configuration an endoscope system. The system illustrated in FIG. 1 includes an endoscope 1 that is inserted into the body of a subject, captures an image, and outputs a video signal to be observed, a processor 2 for an endoscope that converts the video signal output by the endoscope 1 into an endoscopic image, and a display device 3 that displays the endoscopic image and the like. Each device transmits and receives electric signals, video signals, and the like through connectors.

The endoscope 1 is an instrument that includes an insertion portion, which has an imaging element in a tip portion and is inserted into the body of the subject, and is used for diagnosis or treatment. The endoscope 1 transmits the image captured by the imaging element provided at the tip to the processor 2 for an endoscope.

The processor 2 for an endoscope is an information processing device that performs image processing on the captured image acquired from the imaging element provided at the tip of the endoscope 1 to generate an endoscopic image and outputs the endoscopic image to the display device 3. In addition, hereinafter, for the sake of simplicity, the processor 2 for an endoscope is referred to as the processor 2.

The display device 3 is, for example, a liquid crystal display, an organic electroluminescence (EL) display, or the like and displays the endoscopic image or the like output from the processor 2.

Figure 2:
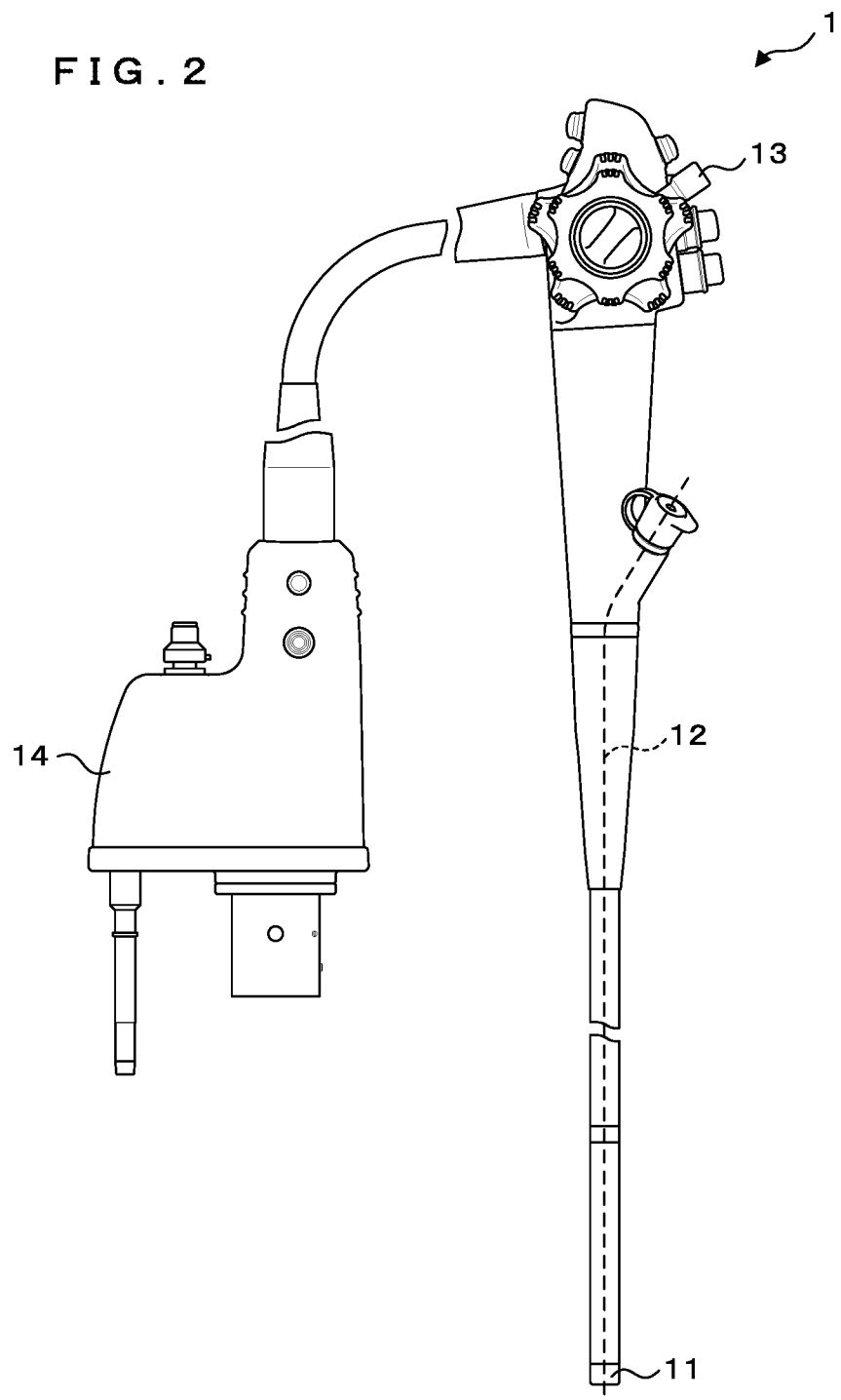
FIG. 2 is a diagram illustrating the outward appearance of an endoscope.

FIG. 2 is a diagram illustrating the outward appearance of the endoscope 1. The endoscope 1 includes an imaging element 11, a treatment tool insertion channel 12, an operation unit 13, and a connector 14. The imaging element 11 is, for example, a charge coupled device (CCD) image sensor, a charge modulation device (CMD) image sensor, or a complementary metal oxide semiconductor (CMOS) image sensor that is installed in the tip portion of the endoscope 1 and performs photoelectric conversion on incident light. A signal processing circuit (not illustrated) performs signal processing, such as A/D conversion and noise removal, on an electric signal generated by the photoelectric conversion and outputs the processed signal to the processor 2.

The treatment tool insertion channel 12 is a channel through which a treatment tool passes. Examples of treatment tool include grippers, biopsy needles, forceps, snares, clamps, scissors, scalpels, incision instruments, endoscopic staplers, tissue loops, clip pliers, suture delivery instruments, energy-based tissue coagulation instruments, or tissue cutting instruments. The operation unit 13 is provided with a release button, an angle knob for bending the tip of the endoscope, and the like and receives the input of operation instruction signals from peripheral devices for air supply, water supply, gas supply, and the like. The connector 14 is connected to the processor 2.

Figure 3:
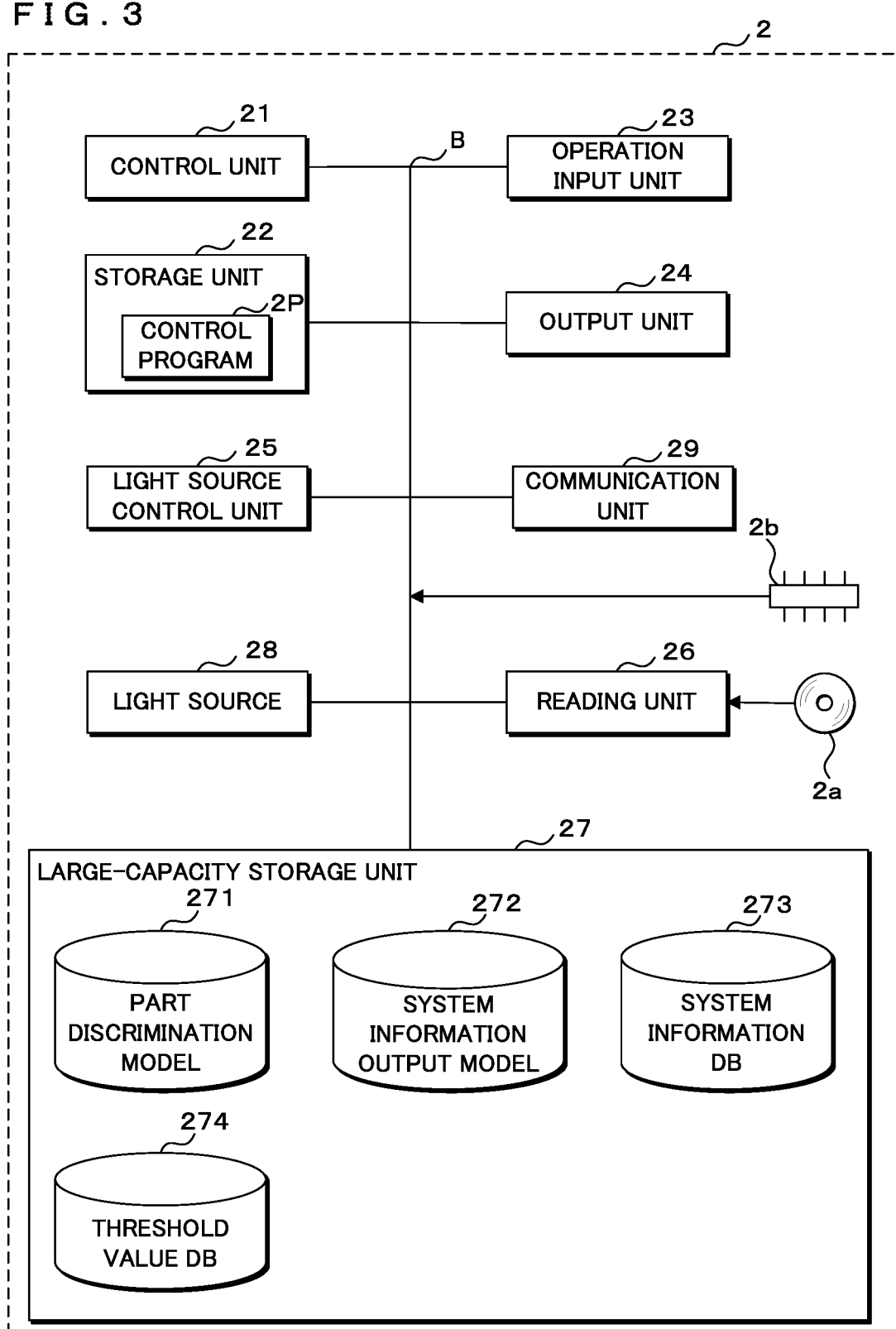
FIG. 3 is a block diagram illustrating an example of the configuration of a processor.

FIG. 3 is a block diagram illustrating an example of the configuration of the processor 2. The processor 2 includes a control unit 21, a storage unit 22, an operation input unit 23, an output unit 24, a light source control unit 25, a reading unit 26, a large-capacity storage unit 27, a light source 28, and a communication unit 29. The components are connected to each other by a bus B.

The control unit 21 includes arithmetic processing units, such as a central processing unit (CPU), a micro-processing unit (MPU), and a graphics processing unit (GPU), reads a control program 2P stored in the storage unit 22, and executes the program 2P to perform various kinds of information processing, a control process, and the like related to the processor 2. In addition, the control unit 21 is described as a single processor in FIG. 3. However, the control unit 21 may be a multiprocessor.

The storage unit 22 includes memory devices, such as a random access memory (RAM) and a read only memory (ROM), and stores the control program 2P or data required for the control unit 21 to execute processes. In addition, the storage unit 22 temporarily stores, for example, data required for the control unit 21 to execute arithmetic processing. The operation input unit 23 includes input devices, such as a touch panel and various switches, and inputs input signals, which have been generated in response to external operations on these input devices, to the control unit 21. The output unit 24 outputs image signals for display and various kinds of information to the display device 3 such that images and information are displayed under the control of the control unit 21.

The light source control unit 25 controls the amount of illumination light emitted by turning on and off LEDs or the like and adjusting a driving current and a driving voltage of the LEDs or the like. In addition, for example, the light source control unit 25 changes an optical filter to control the wavelength band of the illumination light. The light source control unit 25 independently controls the turning-on or turning-off of each LED and the amount of light emitted when each LED is turned on to adjust the emission timing, emission period, amount, and spectrum of the illumination light.

The reading unit 26 reads a portable storage medium 2a including a compact disc (CD)-ROM or a digital versatile disc (DVD)-ROM. The control unit 21 may read the control program 2P from the portable storage medium 2a through the reading unit 26 and store the control program 2P in the large-capacity storage unit 27. In addition, the control unit 21 may download the control program 2P from another computer through a network N or the like and store the control program 2P in the large-capacity storage unit 27. Furthermore, the control unit 21 may read the control program 2P from the semiconductor memory 2b.

The large-capacity storage unit 27 includes, for example, a recording medium such as a hard disk drive (HDD) or a solid state drive (SSD). The large-capacity storage unit 27 stores a part discrimination model (first learning model) 271, a system information output model (second learning model) 272, a system information database (DB) 273, and a threshold value DB 274.

The part discrimination model 271 is a part discriminator that discriminates a part of the subject and is a trained model generated by machine learning. The part of the subject may be, for example, the mouth, the esophagus, the stomach, the small intestine, the large intestine, or the like. The system information output model 272 is an output device that outputs system information and is a trained model generated by machine learning.

The system information DB 273 stores various kinds of system information for setting the system. The threshold value DB 274 stores threshold values of various kinds of system information. In addition, the part discrimination model 271 and the system information output model 272 may be disposed in a cloud computing system that is connected through the network and then used.

In addition, in this embodiment, the storage unit 22 and the large-capacity storage unit 27 may be configured as an integrated storage device. Further, the large-capacity storage unit 27 may be composed of a plurality of storage devices. Furthermore, the large-capacity storage unit 27 may be an external storage device that is connected to the processor 2.

The light source 28 includes a light source that emits illumination light used to illuminate the object to be observed. The light source 28 is, for example, semiconductor light sources, such as a plurality of color light emitting diodes (LEDs) having different wavelength ranges, a combination of a laser diode and a phosphor, a xenon lamp, a halogen lamp, or the like. The light used to illuminate the object to be observed is guided to the tip of the endoscope 1 by an optical fiber. In addition, the light source may be provided at the tip of the endoscope. The light source 28 adjusts, for example, brightness under the control of the light source control unit 25 of the processor 2. Further, in this embodiment, the processor 2 is a light source integrated type. However, the disclosure is not limited thereto. For example, the processor 2 may be a light source separated type that is separated from a light source device. The communication unit 29 is a communication module for performing processes related to communication and transmits and receives information to and from, for example, an external information processing device through the network N.

FIG. 4 is an explanatory diagram illustrating an example of the record layout of the system information DB 273. The system information DB 273 is a database that stores a management ID and system information in association with each other. The system information includes, for example, setting information, such as the intensity of a color (for example, red or blue), brightness (luminance), or an enhancement mode for setting the endoscopic image. Further, the system information includes setting information of a lamp aperture for controlling the brightness of the illumination light and the voltage or current applied to a lamp. The above-described information is an example of the system information.

The system information DB 273 includes a management ID column, an image setting column, a lamp aperture column, and a voltage/current column. The management ID column stores the ID of a management number that is uniquely specified, in order to identify the management number for managing each system information item. The image setting column includes a red column, a blue column, a brightness column, and an enhancement column. The red column stores a set value of the intensity of red in the endoscopic image. The blue column stores a set value of the intensity of blue in the endoscopic image. The brightness column stores setting information of the brightness (luminance) of the endoscopic image. For example, in a case in which the brightness is set to 5 levels, "level 1", "level 2", "level 3", "level 4" or "level 5" may be stored in the brightness column.

The enhancement column stores a setting mode for performing an endoscopic image enhancement process on, for example, a structure or a color. The setting mode may be, for example, "Off", "Low", "Med", or "High". For example, the visibility of blood vessels can be improved by emphasizing a difference in color between mucous membranes and blood vessels using color enhancement that emphasizes a minute change in color. The lamp aperture column stores information for controlling the brightness of the illumination light. The voltage/current column stores the voltage or current applied to the lamp.

FIG. 5 is an explanatory diagram illustrating an example of the record layout of the threshold value DB 274. The threshold value DB 274 includes an item ID column, a category column, an item column, and a threshold value column. The item ID column stores the ID of an item that is uniquely specified, in order to identify each item. The category column stores type information of the item. The item column stores the name of the item. The threshold value column stores a threshold value of the item.

Figure 6:
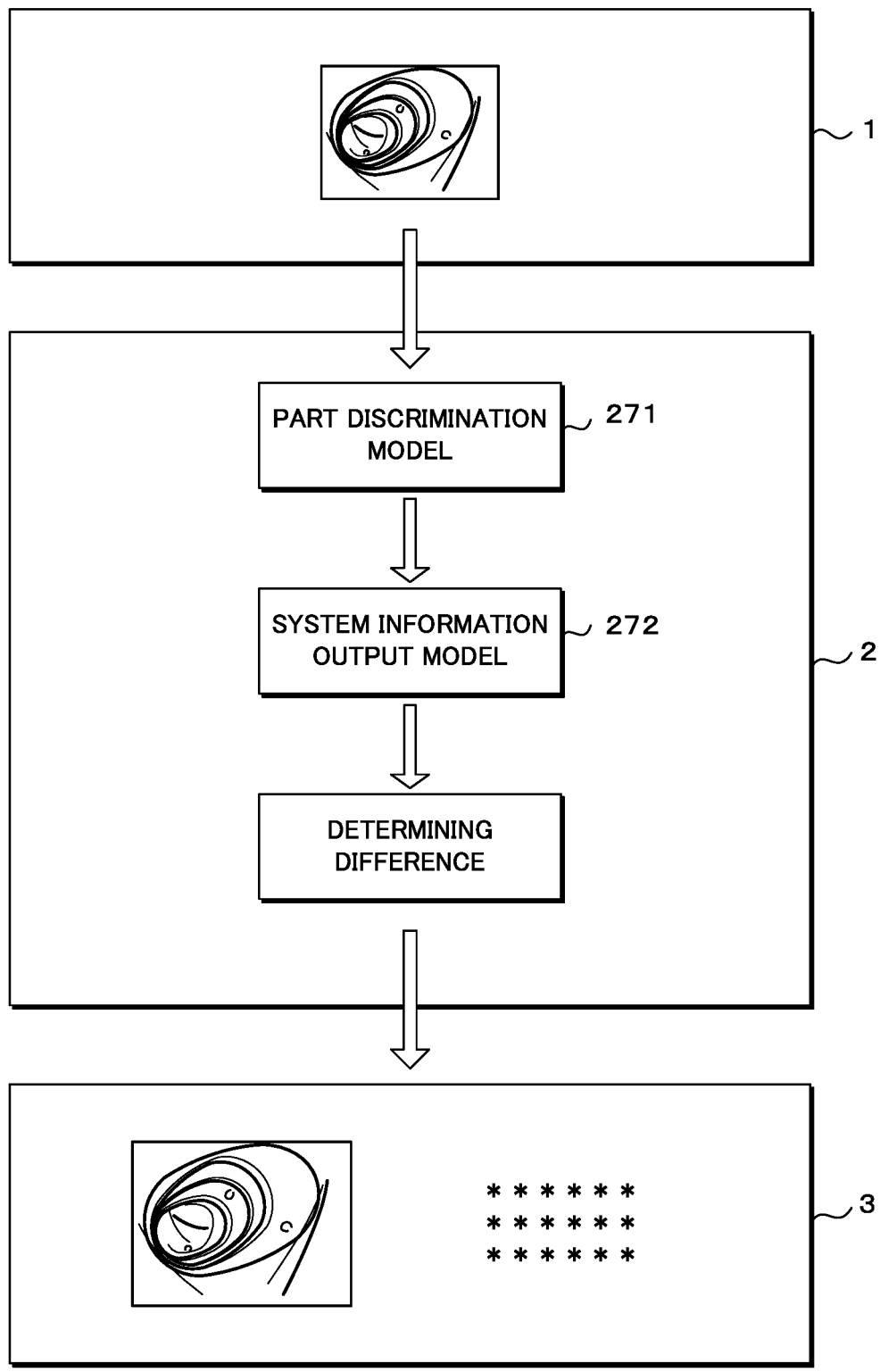
FIG. 6 is an explanatory diagram describing a process of monitoring a system abnormality.

FIG. 6 is an explanatory diagram describing a process of monitoring a system abnormality. In a case in which the tip of the endoscope 1 is inserted into the body of the subject, the control unit 21 of the processor 2 acquires an endoscopic image captured using the first system information from the endoscope 1. The first system information is system information which has been set in the endoscope system that is being used (currently). The user can operate, for example, a keyboard connected to the processor 2 to change the first system information. In a case in which the first system information is changed, the control unit 21 of the processor 2 stores the first system information in the system information DB 273 of the large-capacity storage unit 27. In addition, since items included in the first system information are the same as the items included in the above-mentioned system information, the description thereof will not be repeated.

The control unit 21 calculates parameter on the basis of the acquired endoscopic image. The parameter include a color tone parameter, a brightness parameter, a spatial frequency parameter, or a noise amount parameter of the endoscopic image. The color tone parameter may be, for example, a value obtained by averaging value of R, G, or B pixels values of pixels constituting the endoscopic image within the entire screen or a predetermined range of the screen, or may be the frequency of appearance of the pixel values based on a histogram indicating the overall distribution of the pixel values in the image. R is a pixel value of a red sub-pixel, G is a pixel value of a green sub-pixel, and B is a pixel value of a blue sub-pixel.

The brightness parameter may be, for example, the brightness of each pixel, that is, $((R+G+B)/3)$ or may be the number of pixels corresponding to each brightness value based on a brightness histogram indicating the brightness distribution of the pixels in the image and the degree of bias of the distribution.

The spatial frequency parameter may be, for example, the frequency distribution of image data obtained by the Fourier transform. The spatial frequency indicates the number of repetitions of a pattern included in a unit length. For example, the spatial frequency indicates the number of repetitions of a sinusoidal shading change per unit length for a two-dimensional image. In this case, the spatial frequency is high in the place where shading changes rapidly and is low in the place where the shading changes slowly.

The noise amount parameter is the amount of image noise and is represented by the standard deviation (SD) which is the square root of the variance. The image noise is a high-frequency component having a high spatial frequency in brightness non-uniformity that occurs in the captured image. The standard deviation is represented by a value indicating the degree of scattering of data.

The control unit 21 acquires the type information of the endoscope 1. The type information includes, for example, the series and model number of the endoscope, the number of pixels of the imaging element, and target part information (for example, the upper gastrointestinal tract). The control unit 21 acquires the type information from the endoscope 1 (scope). Alternatively, in a case in which type information corresponding to each model number is stored in the storage unit 22 in advance, the control unit 21 acquires the model number from the endoscope 1. The control unit 21 may acquire type information corresponding to the acquired model number from the storage unit 22.

The control unit 21 discriminates the part of the subject using the part discrimination model 271 that outputs the discrimination result of discriminating the part of the subject in a case in which the parameter calculated on the basis of the endoscopic image and the acquired type information are input. In addition, a part discrimination process will be described below.

The control unit 21 acquires (outputs) the second system information using the system information output model 272 that outputs the second system information in a case in which the parameter calculated on the basis of the endoscopic image, the acquired type information, and the discriminated part of the subject are input. In addition, since items included in the second system information are the same as the items included in the first system information, the description thereof will not be repeated. A process of acquiring the second system information will be described below.

The control unit 21 acquires the first system information from the system information DB 273 of the large-capacity storage unit 27. The control unit 21 compares the acquired first system information with the second system information to determine the difference. Specifically, the control unit 21 compares each item of the first system information with each corresponding item of the second system information for the setting information of the intensity of red, intensity of blue, and brightness of the image, the setting information of the enhancement mode, the setting information of the lamp aperture, and the voltage or current applied to the lamp.

In a case in which the control unit 21 determines that the two information items are matched with each other, it determines that no abnormality has been detected. In a case in which the control unit 21 determines that the two information items are not matched with each other, it determines whether or not the system settings can be changed. Specifically, the control unit 21 acquires the threshold value of the system information from the threshold value DB 274 of the large-capacity storage unit 27. The control unit 21 determines whether or not each item of the second system information is within a threshold value range on the basis of the acquired threshold value.

In a case in which the control unit 21 determines that each item or some items of the second system information are out of the threshold value range, it outputs a message including the fact that the difference has been detected to the display device 3. In a case in which the control unit 21 determines that each item of the second system information is within the threshold value range, it changes the system settings using the first system information. For example, in an example in which the intensity of red in the first system information is set to "2", in a case in which the control unit 21 determines that the intensity of red in the second system information is "3", it changes the intensity setting of red in the system to "2".

In addition, for example, in a case in which the control unit 21 determines that the value of the lamp aperture in the second system information is smaller than the value of the lamp aperture in the first system information, there is a possibility that the amount of light will be less than that in a normal state due to an abnormality in a light source system. In this case, the control unit 21 changes the value of the lamp aperture in the system to the value of the lamp aperture in the first system information in order to increase the value of the lamp aperture in the system.

In a case in which the control unit 21 determines that the change of the system settings has succeeded, it outputs a message including the fact that the change has succeeded to the display device 3. In addition, before the system settings are changed, a setting change confirmation message may be output to the user (doctor). In this case, the system settings are changed with the consent of the user. In a case in which the control unit 21 determines that the change of the system settings has failed, it outputs a message including the fact that the change has failed to the display device 3.

Figure 7:
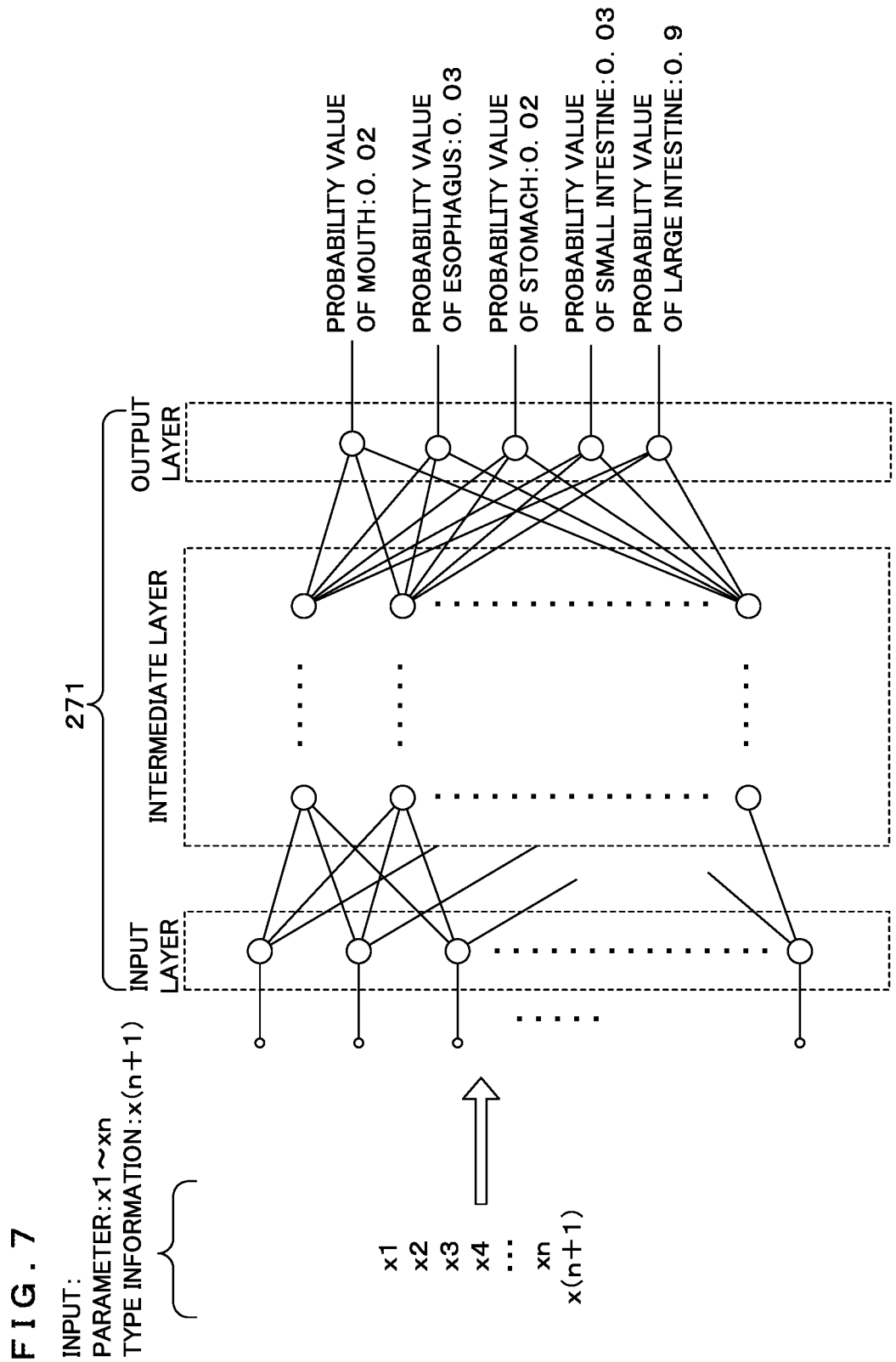
FIG. 7 is an explanatory diagram describing a part discrimination model.

Then, the part discrimination process using the part discrimination model 271 will be described. FIG. 7 is an explanatory diagram describing the part discrimination model 271. The part discrimination model 271 is used as a program module which is a portion of artificial intelligence software. The part discrimination model 271 is a discriminator in which a neural network that receives parameter calculated on the basis of an endoscopic image and type information as an input and outputs the result of predicting a part of the subject has been constructed (generated).

The neural network is, for example, a convolutional neural network (CNN) and includes a input layer that receives the input of the parameter calculated on the basis of the endoscopic image and the type information, an output layer that outputs the result of predicting a part of the subject, and an intermediate layer that has been trained by backpropagation. Each layer has one or more neurons (nodes), and each neuron has a value. Then, the neurons between one layer and the next layer are connected by edges, and each edge has variables (or parameter) such as weights or biases.

In the CNN, the value of the neuron in each layer is calculated by performing predetermined computation based on, for example, the value of the neuron in the previous layer and the weight of the edge. Then, when the input data is input to the neuron of the input layer, the value of the neuron in the next layer is calculated by predetermined computation. Further, when the data calculated by computation is input, the value of the neuron in the next layer is calculated by predetermined computation in the layer. Then, the value of the neuron in the output layer which is the last layer becomes output data with respect to the input data.

Further, in this embodiment, the part discrimination model 271 is described as the CNN. However, the part discrimination model 271 is not limited to the CNN and may be a neural network other than the CNN, Regions with Convolutional Neural Networks (R-CNN), Support Vector Machine (SVM), a Bayesian network, or a trained model constructed by any learning algorithm such as a regression tree.

The control unit 21 compares the discrimination result output from the output layer with the labeled information of the part with respect to training data, that is, a correct answer value and optimizes variables used for arithmetic processing in the intermediate layer such that an output value from the output layer is close to the correct answer value. The training data is data that is generated by associating the name of a part (for example, the large intestine) with the parameter calculated on the basis of the endoscopic image and the type information of the endoscope 1. The variables include, for example, a weight (connection coefficient) between neurons and a coefficient of an activation function used in each neuron. A method for optimizing the variables is not particularly limited. For example, the control unit 21 optimizes various variables using a backpropagation method.

The control unit 21 performs the above-described process on parameter and type information included in the training data to generate the part discrimination model 271. In addition, a process of generating the part discrimination model 271 is not limited to the above-mentioned process. For example, the control unit 21 may generate the part discrimination model for each type of endoscope. For example, the control unit 21 may generate a large intestine discrimination model for discriminating the large intestine.

In this embodiment, an example in which the part discrimination model 271 is generated by the processor 2 has been described. However, the disclosure is not limited to this example. For example, the part discrimination model 271 may be generated by an external device (for example, a server or the like).

In this case, the control unit 21 of the processor 2 may download the part discrimination model 271 generated by the external device using the communication unit 29 and install the part discrimination model 271. In addition, the control unit 21 may read the part discrimination model 271 generated by the external device from the portable storage medium 2a or the semiconductor memory 2b through the reading unit 26 and install the part discrimination model 271. Further, the processor 2 or an external device may perform the process of updating the part discrimination model 271.

In a case in which the control unit 21 acquires the endoscopic image from the endoscope 1, it discriminates the part of the subject using the part discrimination model 271. As illustrated in FIG. 7, the input layer of the part discrimination model 271 receives the input of parameters "x1 to xn" calculated on the basis of the endoscopic image and type information "x(n+1)". x1 to xn indicate the color tone parameter, the brightness parameter, the spatial frequency parameter, or the noise amount parameter of the above-mentioned endoscopic image. x(n+1) indicates type information including the series and model number of the endoscope, the number of pixels of the imaging element, or target part information.

In addition, in the above-described various parameters, in a case in which the average value of R, G, or B pixels values of pixels constituting the endoscopic image, the degree of bias of the distribution based on the histogram, or the spatial frequency is input to the part discrimination model 271, the parameter has a great influence on the discrimination result of the part of the subject.

The intermediate layer changes the number of dimensions of input information input from the input layer to extract the features of the input information. Then, the intermediate layer predicts the probability that the endoscopic image will be each part of the subject corresponding to the extracted features using a fully connected layer that has learned parameter using backpropagation. The prediction result is output to the output layer having a plurality of neurons. As illustrated in FIG. 7, the prediction result indicating that the probability value of the mouth is 0.02, the probability value of the esophagus is 0.03, the probability value of the stomach is 0.02, the probability value of the small intestine is 0.03, and the probability value of the large intestine is 0.9 is output.

In addition, the part discrimination process is not limited to the process of discriminating the part using machine learning. For example, the control unit 21 of the processor 2 may discriminate the part from the endoscopic image, using a local feature amount extraction method, such as Accelerated KAZE (A-KAZE) or Scale Invariant Feature Transform (SIFT), on the basis of a change in the color or fold of each part. Alternatively, the control unit 21 of the processor 2 may receive the discrimination result of the part of the subject by the doctor on the basis of medical expertise through the operation input unit 23.

Figure 8:
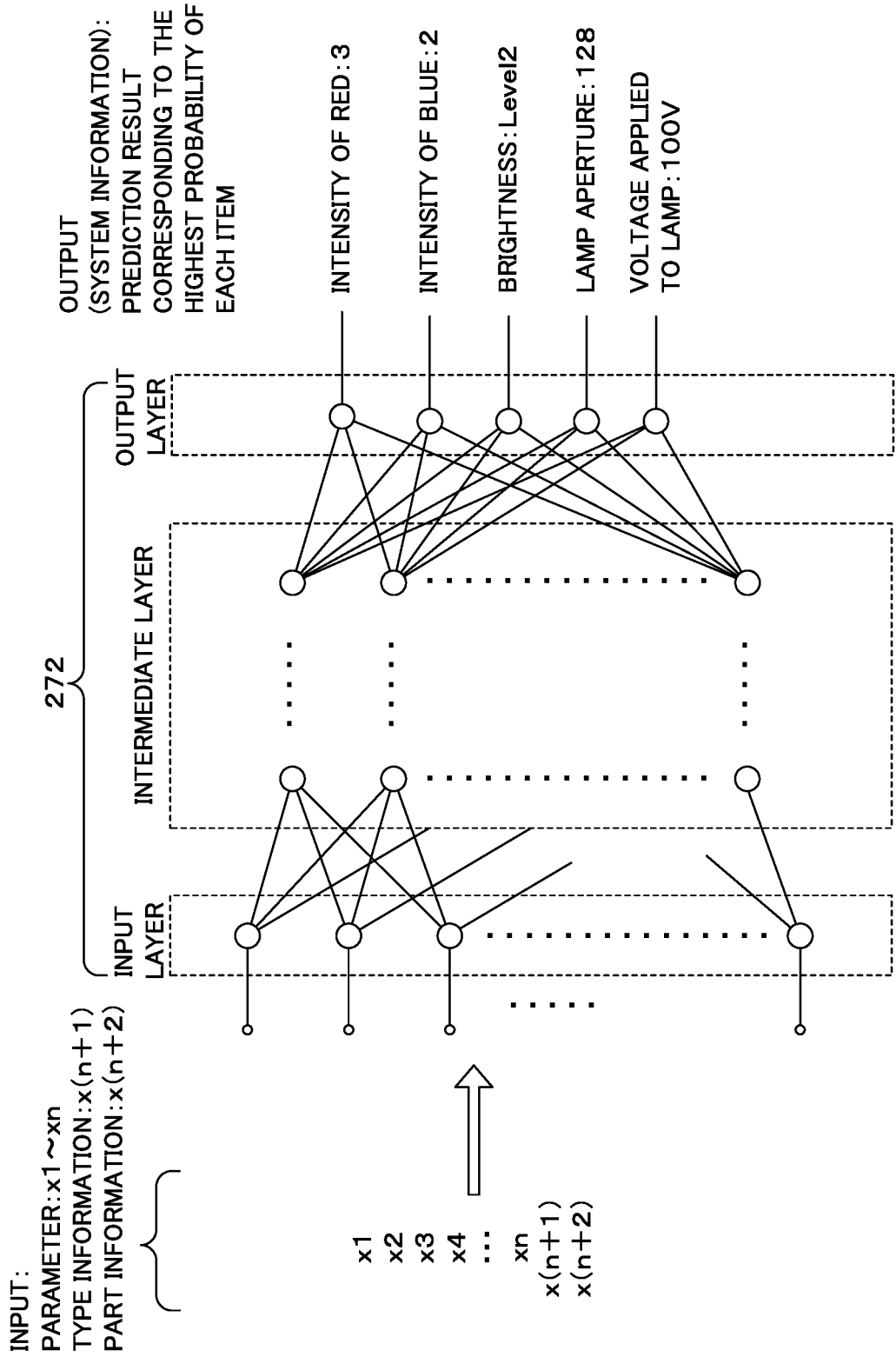
FIG. 8 is an explanatory diagram describing a system information output model.

Next, the process of acquiring the second system information using the system information output model 272 will be described. FIG. 8 is an explanatory diagram describing the system information output model 272. The system information output model 272 is used as a program module that is a portion of artificial intelligence software.

The system information output model 272 is an output device in which a neural network that receives the parameter calculated on the basis of the endoscopic image, the type information and the part of the subject (the discrimination result of the part) output from the part discrimination model 271 as an input and outputs the result of predicting the second system information has been constructed (generated). Hereinafter, an example in which the neural network is a CNN will be described. In addition, since the configuration of the system information output model 272 in the CNN is the same as the configuration of the part discrimination model 271, the description thereof will not be repeated.

In addition, in this embodiment, the system information output model 272 is described as a CNN. However, the system information output model 272 is not limited to the CNN and may be a neural network other than the CNN, an R-CNN, an SVM, a Bayesian network, or a trained model constructed by any learning algorithm such as a regression tree.

The control unit 21 compares the prediction result output from an output layer with the labeled information of each item of the system information with respect to the training data, that is, the correct answer value and optimizes the variables used for arithmetic processing in an intermediate layer such that the output value from the output layer is close to the correct answer value. The training data is data generated by associating each item of the system information with the parameter calculated on the basis of the endoscopic image, the type information of the endoscope 1, and the part of the subject. The control unit 21 performs the above-described process on the parameter and various kinds of information included in the training data to generate the system information output model 272.

Further, the process of generating the system information output model 272 is not limited to the above-described process. For example, the control unit 21 may generate the system information output model for each type of endoscope or may generate the system information output model for each part of the subject. Furthermore, the control unit 21 may generate the system information output model for each item of the system information. For example, the control unit 21 may generate a color intensity determination model for determining the intensity of red or blue of the image, a brightness determination model for determining the brightness of the image, or the like.

Moreover, in this embodiment, an example in which the system information output model 272 is generated by the processor 2 has been described. However, the disclosure is not limited to this example. For example, the system information output model 272 may be generated by an external device.

In a case in which the control unit 21 acquires the part of the subject using the part discrimination model 271, it acquires the second system information using the system information output model 272. As illustrated in FIG. 8, the input layer of the system information output model 272 receives the input of parameters "x1 to xn" calculated on the basis of the endoscopic image, type information "x(n+1)", and a part "x(n+2)" of the subject output from the part discrimination model 271. Since x1 to xn and x(n+1) are the same as the above-described input information, the description thereof will not be repeated. x(n+2) indicates a part (for example, the large intestine) of the subject.

In addition, in the above-described various parameters, in a case in which the frequency of appearance of the pixel values based on a histogram, the average value of brightness, or the amount of noise (standard deviation) is input to the system information output model 272, the parameter has a great influence on the output result of the second system information.

The intermediate layer changes the number of dimensions of input information input from the input layer to extract the features of the input information. Then, the intermediate layer predicts the probability of each item of the second system information corresponding to the extracted features, using the fully connected layer that has learned parameter using backpropagation. The prediction result is output to the output layer having a plurality of neurons. As illustrated in FIG. 8, the prediction result corresponding to the highest probability of each item of the second system information is output. In addition, the disclosure is not limited to the above-described output result, and all probability values of each item of the system information may be output.

Further, the probability values of combinations of the items of the system information may be output. For example, the probability values of "the intensity of red: 3, the intensity of blue: 2, the brightness: Level 2, the lamp aperture: 128, and the voltage applied to the lamp: 100 V" may be output. Furthermore, in addition to outputting the probability values of all combinations, a combination corresponding to the highest probability among the probability values of the combinations may be output as the prediction result.

Figure 9:
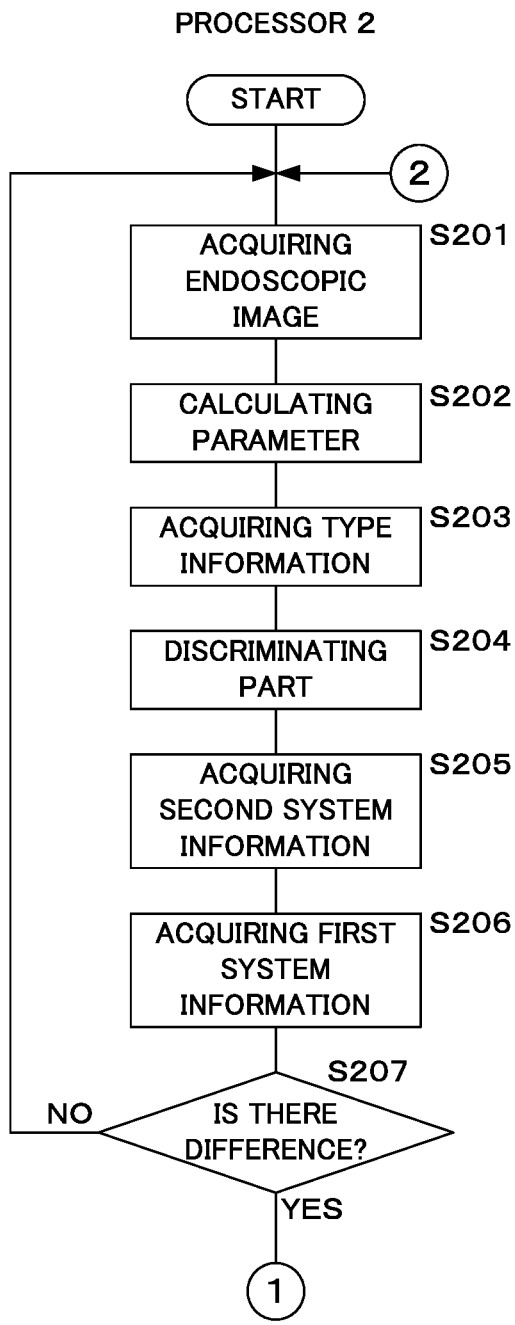
FIG. 9 is a flowchart illustrating a processing procedure when a system abnormality is monitored.
Figure 10:
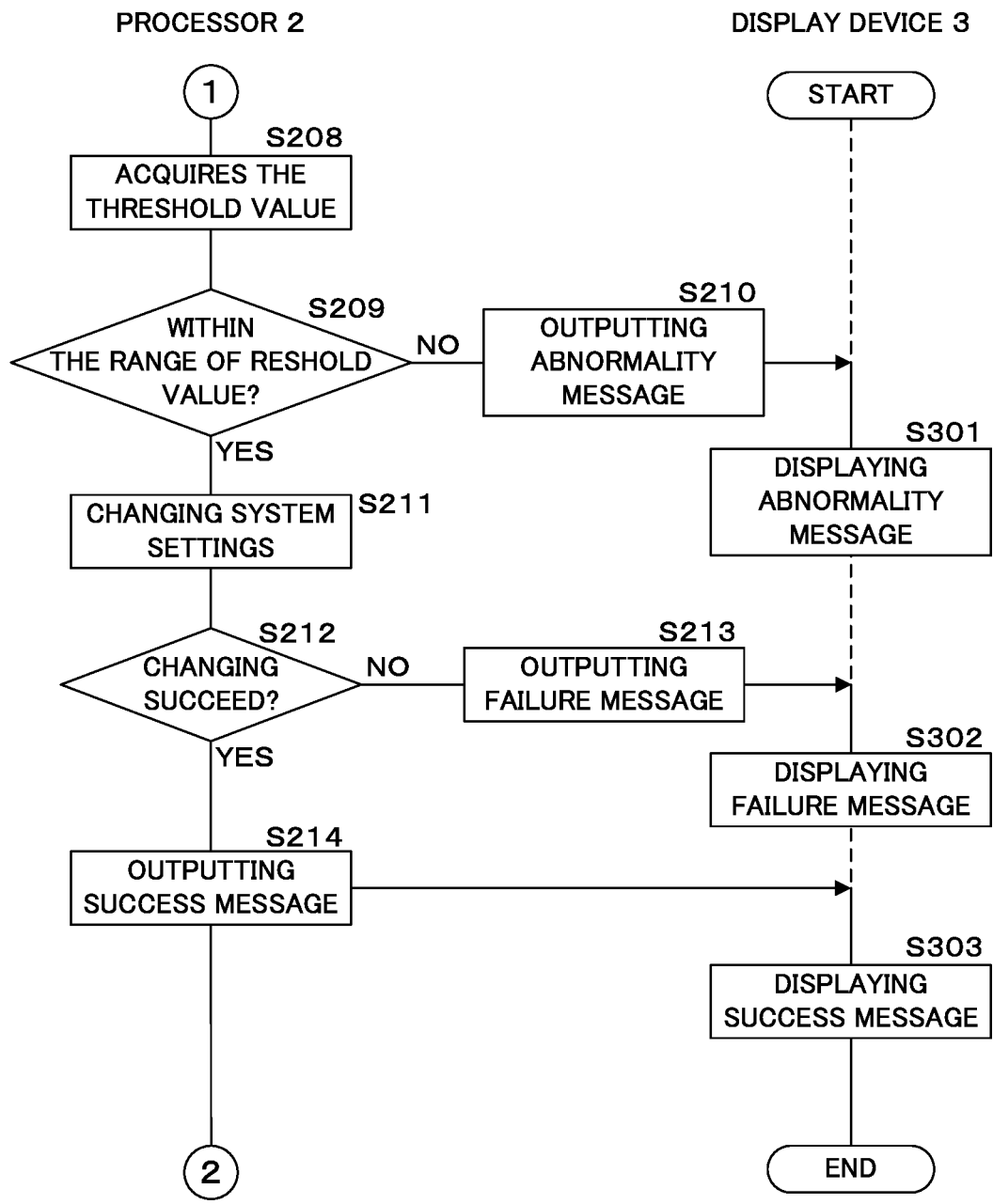
FIG. 10 is a flowchart illustrating the processing procedure when the system abnormality is monitored.

FIGS. 9 and 10 are flowcharts illustrating a processing procedure when a system abnormality is monitored. The control unit 21 of the processor 2 acquires the endoscopic image captured using the first system information from the endoscope 1 (Step S201). The control unit 21 calculates parameter on the basis of the acquired endoscopic image (Step S202). The control unit 21 acquires type information including, for example, the series and model number of the endoscope, the number of pixels of the imaging element, and target part information stored in the endoscope 1 in advance (Step S203).

The control unit 21 discriminates the part of the subject using the part discrimination model 271 that outputs the discrimination result of discriminating the part of the subject in a case in which the parameter calculated on the basis of the endoscopic image and the acquired type information are input (Step S204). The control unit 21 acquires the second system information using the system information output model 272 that outputs the second system information in a case in which the parameter calculated on the basis of the endoscopic image, the acquired type information, and the part of the subject discriminated by the part discrimination model 271 are input (Step S205).

The control unit 21 acquires the first system information including the setting information of the intensity of red, intensity of blue, and brightness of the image, the setting information of the enhancement mode, the setting information of the lamp aperture, and the voltage or current applied to the lamp from the system information DB 273 of the large-capacity storage unit 27 (Step S206). The control unit 21 compares each item of the acquired first system information with each corresponding item of the second system information to determine the difference (Step S207).

In a case in which the control unit 21 determines that there is no difference between the first system information and the second system information (NO in Step S207), it returns to Step S201. In a case in which the control unit 21 determines that there is a difference between the first system information and the second system information (YES in Step S207), it acquires the threshold value of the system information from the threshold value DB 274 of the large-capacity storage unit 27 (Step S208). The control unit 21 determines whether or not each item of the second system information is within the range of the threshold value on the basis of the acquired threshold value (Step S209).

In a case in which the control unit 21 determines that each item or some items of the second system information are out of the range of the threshold value (NO in Step S209), it outputs an abnormality message including the fact that a difference has been detected to the display device 3 (Step S210). The display device 3 displays the abnormality message output from the processor 2 (Step S301). In a case in which the control unit 21 of the processor 2 determines that each item of the second system information is within the range of the threshold value (YES in Step S209), it changes the system settings using the first system information (Step S211).

In a case in which the control unit 21 determines whether or not the change of the system settings has succeeded (Step S212). In a case in which the control unit 21 determines that the change of the system settings has not succeeded (NO in Step S212), it outputs a message including the fact that the change has failed to the display device 3 (Step S213). The display device 3 displays the message including the fact that the change has failed which has been output from the processor 2 (Step S302).

In a case in which the control unit 21 of the processor 2 determines that the change of the system settings has succeeded (YES in Step S212), it outputs a message including the fact that the change has succeeded to the display device 3 (Step S214). The control unit 21 returns to Step S201. The display device 3 displays the message including the fact that the change has succeeded which has been output from the processor 2 (Step S303).

Figure 11A:
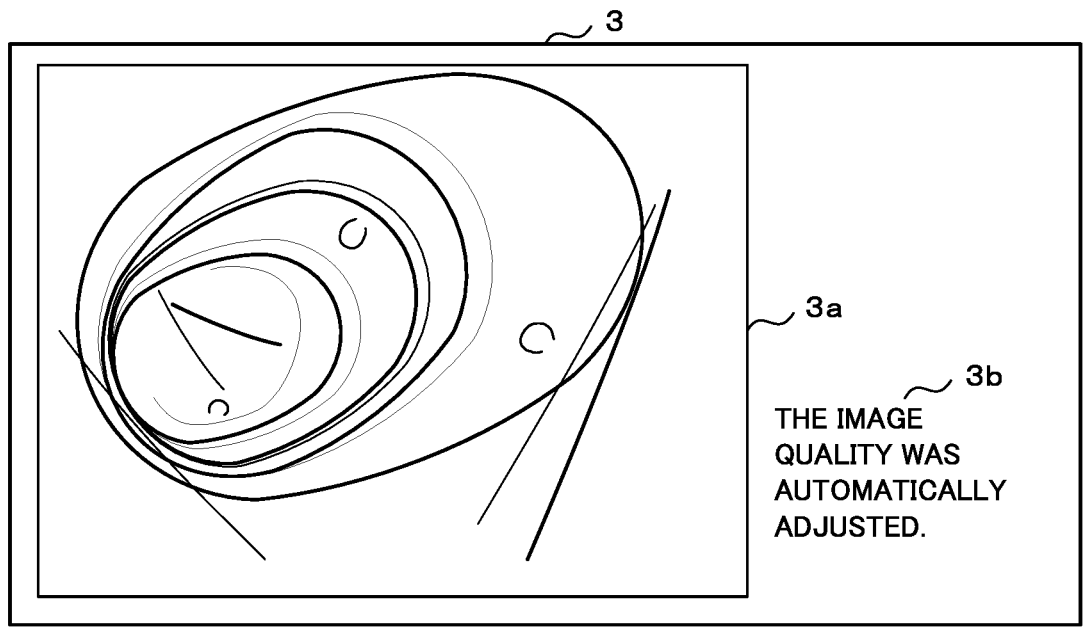
FIG. 11A is a schematic diagram illustrating an endoscopic image on which a message is displayed by a display device.
Figure 11B:
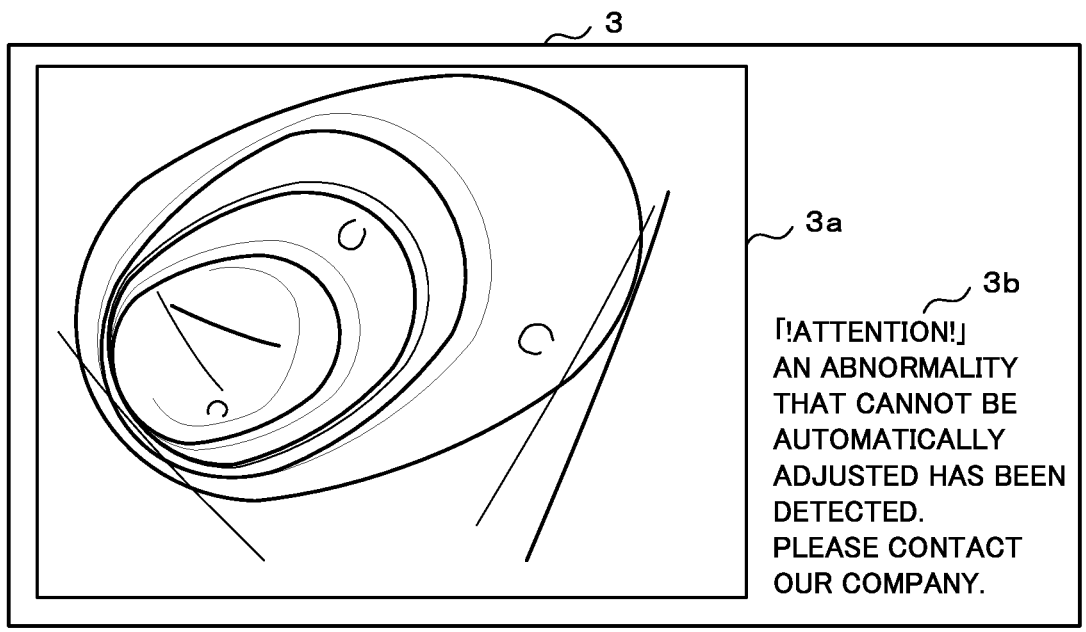
FIG. 11B is a schematic diagram illustrating the endoscopic image on which the message is displayed by the display device.

FIGS. 11A and 11B are schematic diagrams illustrating the endoscopic image on which the message is displayed by the display device 3. Observation screen 3a is an observation screen (region) of the endoscope. Region 3b is a message display region. The display device 3 displays the endoscopic image output from the processor 2 on the observation screen 3a and displays the message output from the processor 2 in the region 3b. In addition, a message display screen is not limited to the above-described layout. For example, the message may be displayed so as to be superimposed on the observation screen 3a of the endoscope. As illustrated in the drawings, FIG. 11A illustrates an example in which, in a case in which the change of the system settings has succeeded, the message including the fact that the change has succeeded is displayed. FIG. 11B illustrates an example in which, in a case in which the change of the system settings has failed, the message including the fact that the change has failed is displayed.

According to this embodiment, a system abnormality is monitored using the learning model, which makes it possible to infer factors that affect image quality. Therefore, it is possible to change the system settings according to the inferred factors.

According to this embodiment, it is possible to specify the cause of a system abnormality using a learning model which has been trained.

According to this embodiment, a message indicating an abnormality which makes it difficult to change the system settings is output. Therefore, it is possible to quickly respond when a failure occurs.

According to this embodiment, system information is output in a case in which various parameters, such as image settings, an optical system, a light source, and electricity, that affect image quality are input to a learning model. Therefore, it becomes possible to monitor abnormalities that are not noticed.

Embodiment 2

Embodiment 2 relates to an aspect in which a part of a subject is discriminated using an image feature amount. In addition, the description of the same content as that in Embodiment 1 will not be repeated. The image feature amount is image geometric values of each region of an image and a numerical value of a feature parameter calculated from these values and is obtained by applying an image processing method. For example, the image feature amount may be the average value of R, G, or B pixels values of pixels constituting the image, the average value of brightness, the degree of bias of brightness, or the like.

In Embodiment 1, in a case in which the parameter calculated on the basis of the endoscopic image is input to the part discrimination model 271, the discrimination result of discriminating the part of the subject is output. However, the disclosure is not limited thereto. In this embodiment, a process of outputting the discrimination result of discriminating the part of the subject in a case in which the endoscopic image captured using the first system information is directly input to the part discrimination model 271 will be described.

FIG. 12 is an explanatory diagram describing the part discrimination model 271 according to Embodiment 2. The part discrimination model 271 is a discriminator in which a neural network that receives the endoscopic image captured using the first system information as an input and outputs the result of predicting a part of a subject has been constructed. The neural network is, for example, a CNN and includes an input layer that receives the input of the endoscopic image, an output layer that outputs the result of predicting the part of the subject, and an intermediate layer that has been trained by backpropagation.

The input layer has a plurality of neurons that receive the input of the pixel values of each pixel included in the endoscopic image and transmits the input pixel values to the intermediate layer. The intermediate layer has a plurality of neurons that extract the image feature amount of the endoscopic image and transmits the extracted image feature amount to the output layer. The intermediate layer finally extracts the feature amount of the image while compressing the pixel information of the endoscopic image, using a configuration in which a convolution layer that convolves the pixel values of each pixel input from the input layer and a pooling layer that maps the pixel values convolved by the convolution layer are alternately connected. Then, the intermediate layer predicts the probability that the endoscopic image will be each part of the subject, using a fully connected layer that has learned the parameter using backpropagation. The prediction result is output to the output layer having a plurality of neurons.

In addition, the endoscopic image may pass through the convolution layer and the pooling layer which are alternately connected such that the feature amount thereof is extracted. Then, the endoscopic image may be input to the input layer.

Furthermore, the image input to the part discrimination model 271 is not limited to the endoscopic image. For example, as preprocessing, the control unit 21 generates a histogram image indicating the overall distribution of pixel values in the image, a brightness histogram image indicating the brightness distribution of the pixels in the image, a graph image indicating a spatial frequency, or the like on the basis of the endoscopic image. The control unit 21 inputs the generated graph image to the part discrimination model 271, which has been trained by deep learning using the graph image included in the training data, and outputs the discrimination result of discriminating the part of the subject.

In this embodiment, an example in which the part of the subject is discriminated using the image feature amount has been described. However, this is also applied to a process of outputting the system information. Specifically, the input layer of the system information output model 272 receives the input of the pixel values of each pixel included in the endoscopic image and the part of the subject output from the part discrimination model 271 and transmits the pixel values and the part to the intermediate layer. The intermediate layer extracts the image feature amount of the endoscopic image on the basis of the transmitted pixel values of each pixel. The intermediate layer predicts the probability of each item of the system information on the basis of the part of the subject and the extracted image feature amount and outputs the prediction result to the output layer.

According to this embodiment, it is possible to discriminate the part of the subject through the learning model using the image feature amount of the endoscopic image.

Embodiment 3

Embodiment 3 relates to an aspect in which an information processing device 4 monitors a system abnormality using artificial intelligence. The description of the same content as that in Embodiments 1 and 2 will not be repeated. In Embodiment 1 or 2, the processor 2 performs the part discrimination process and the second system information output process using the learning model. However, in this embodiment, an aspect in which the above-described processes are performed by the information processing device 4 will be described.

The information processing device 4 is an information processing device that constructs a learning model, determines a system abnormality using the learning model, and performs the processing, storage, transmission, and reception of various kinds of information. The information processing device 4 is, for example, a server device, a personal computer, a general-purpose tablet PC (personal computer), or the like.

Figure 13:
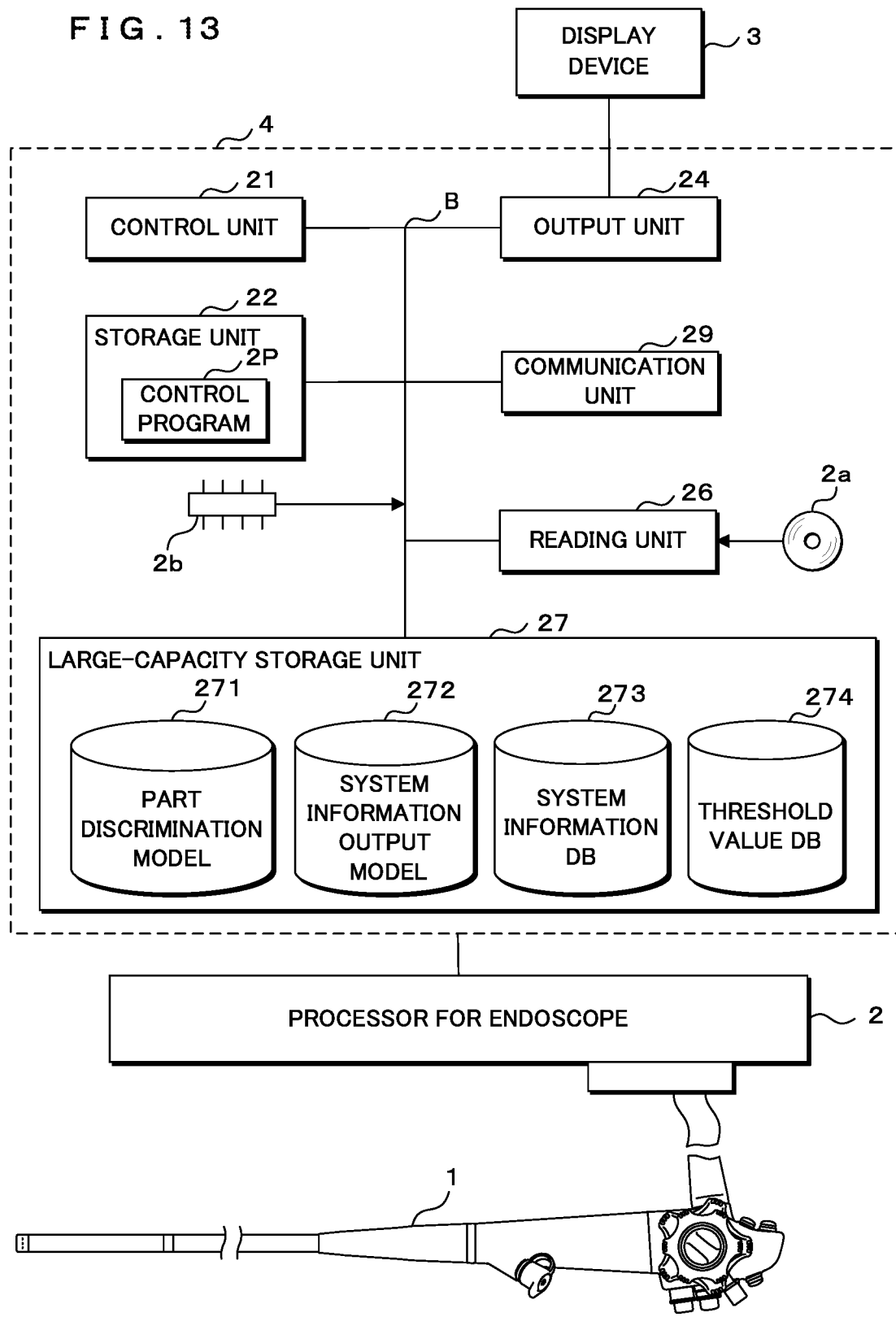
FIG. 13 is a schematic diagram illustrating an example of the configuration of an endoscope system according to Embodiment 3.

FIG. 13 is a schematic diagram illustrating an example of the configuration of an endoscope system according to Embodiment 3. In addition, the same content as that in FIGS. 1 and 3 is denoted by the same reference numeral, and the description thereof will not be repeated. The system illustrated in FIG. 13 includes an endoscope 1, a processor 2, a display device 3, and the information processing device 4. Each device transmits and receives electric signals, video signals, and the like through connectors.

The processor 2 acquires the first system information set in the endoscope system in use, the type information of the endoscope which has been stored in the endoscope 1 in advance, and the endoscopic image captured using the first system information. The processor 2 outputs the acquired first system information, type information, and endoscopic image to the information processing device 4.

A control unit 21 of the information processing device 4 calculates parameter on the basis of the endoscopic image output from the processor 2. The control unit 21 discriminates the part of the subject using the part discrimination model 271 that outputs the discrimination result of discriminating the part of the subject in a case in which the parameter calculated on the basis of the endoscopic image and the type information are input. In addition, since a part discrimination process is the same as that in Embodiment 1 or 2, the description thereof will not be repeated.

The control unit 21 acquires the second system information, using the system information output model 272 that outputs the second system information in a case in which the parameter calculated on the basis of the endoscopic image, the type information, and the part of the subject discriminated by the part discrimination model 271 are input. In addition, since a process of acquiring the second system information is the same as that in Embodiment 1 or 2, the description thereof will not be repeated.

The control unit 21 compares each item of the first system information with each corresponding item of the second system information to determine the difference. In a case in which the control unit 21 determines that there is a difference between the first system information and the second system information, it acquires a threshold value of the system information from the threshold value DB 274 of the large-capacity storage unit 27. The control unit 21 determines whether or not each item of the second system information is within the range of the threshold value on the basis of the acquired threshold value.

In a case in which the control unit 21 determines that each item or some items of the second system information are out of the range of the threshold value, it outputs an abnormality message including the fact that the difference has been detected to the display device 3. In a case in which the control unit 21 determines that each item of the second system information is within the range of the threshold value, it outputs a system setting change notification to the processor 2. The processor 2 changes the system settings using the first system information in response to the system setting change notification output from the information processing device 4.

The processor 2 outputs the result (for example, success or failure) of changing the system settings to the information processing device 4. The control unit 21 of the information processing device 4 outputs an appropriately message to the display device 3 according to the setting change result output from the processor 2.

Figure 14:
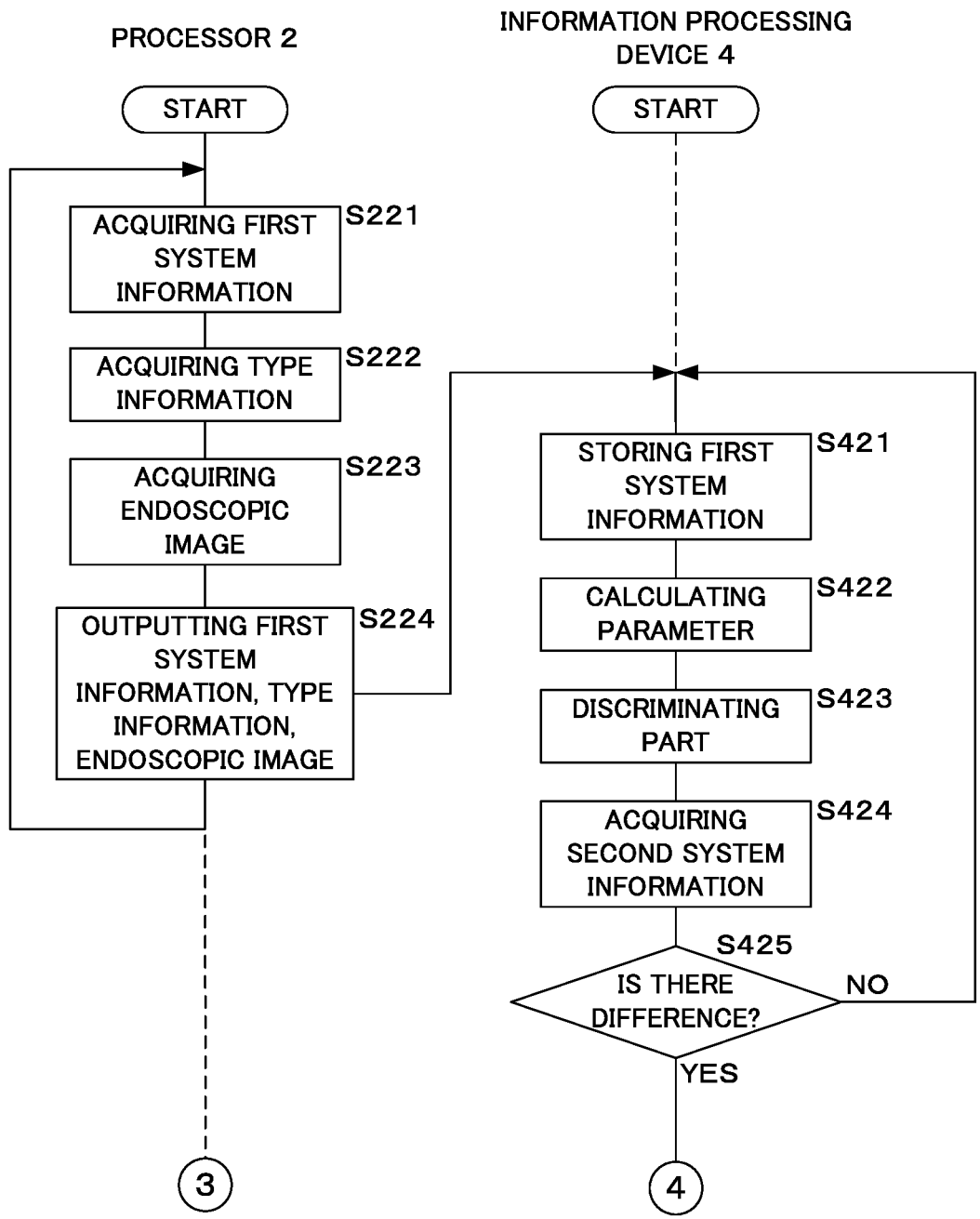
FIG. 14 is a flowchart illustrating a processing procedure when a system abnormality is monitored by an information processing device.
Figure 15:
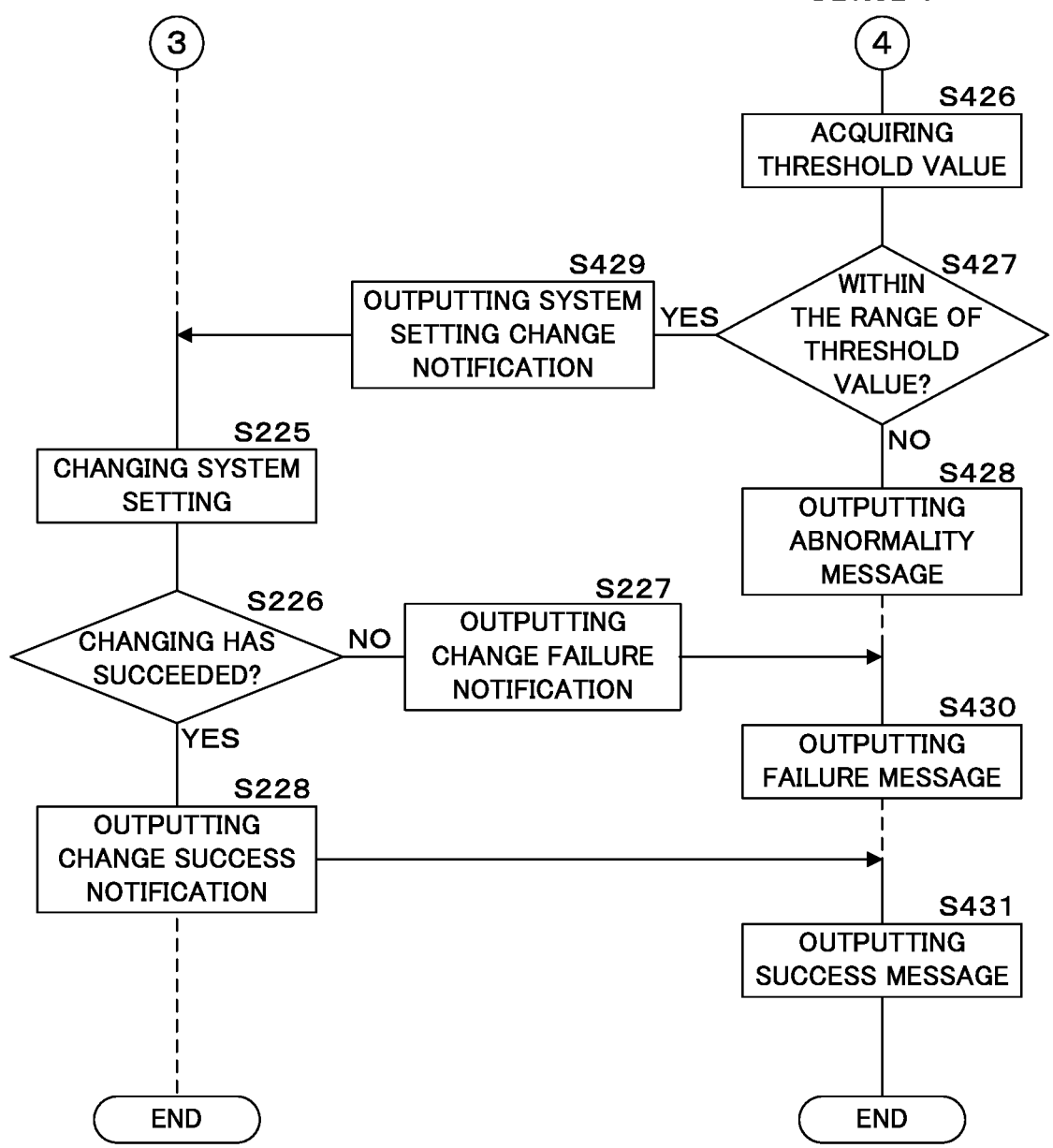
FIG. 15 is a flowchart illustrating the processing procedure when the system abnormality is monitored by the information processing device.

FIGS. 14 and 15 are flowcharts illustrating a processing procedure when the information processing device 4 monitors a system abnormality. The processor 2 acquires the first system information stored in the endoscope system in normal use (Step S221). The control unit 21 acquires the endoscope type information stored in the endoscope 1 in advance (Step S222).

The processor 2 acquires the endoscopic image captured using the first system information from the endoscope 1 (Step S223). The processor 2 outputs the acquired first system information, type information, and endoscopic image to the information processing device 4 (Step S224). The processor 2 returns to Step S221. The control unit 21 of the information processing device 4 stores the first system information output from the processor 2 in the system information DB 273 of the large-capacity storage unit 27 (Step S421).

In addition, in this embodiment, the processor 2 outputs the first system information and the type information to the information processing device 4. However, the disclosure is not limited thereto. For example, the first system information and the type information may be stored in advance in the storage unit 22 or the large-capacity storage unit 27 of the information processing device 4.

The control unit 21 of the information processing device 4 calculates the parameter on the basis of the endoscopic image output from the processor 2 (Step S422). The control unit 21 discriminates the part of the subject using the part discrimination model 271 that outputs the discrimination result of discriminating the part of the subject in a case in which the parameter calculated on the basis of the endoscopic image and the type information output from the processor 2 are input (Step S423).

The control unit 21 acquires the second system information, using the system information output model 272 that outputs the second system information in a case in which the parameter calculated on the basis of the endoscopic image, the type information, and the part of the subject discriminated by the part discrimination model 271 are input (Step S424).

The control unit 21 compares each item of the first system information with each corresponding item of the second system information to determine the difference (Step S425). In a case in which the control unit 21 determines that there is no difference between the first system information and the second system information (NO in Step S425), it returns to Step S421. In a case in which the control unit 21 determines that there is a difference between the first system information and the second system information (YES in Step S425), it acquires the threshold value of the system information from the threshold value DB 274 of the large-capacity storage unit 27 (Step S426).

The control unit 21 determines whether or not each item of the second system information is within the range of the threshold value on the basis of the acquired threshold value (Step S427). In a case in which the control unit 21 determines that each item or some items of the second system information are out of the range of the threshold value (NO in Step S427), it outputs an abnormality message including the fact that a difference has been detected to the display device 3 (Step S428).

In a case in which the control unit 21 determines that each item of the second system information is within the range of the threshold value (YES in Step S427), it outputs a system setting change notification to the processor 2 (Step S429). The processor 2 changes the system settings using the first system information in response to the system setting change notification output from the information processing device 4 (Step S225).

The processor 2 determines whether the change of the system settings has succeeded or failed (Step S226). In a case in which the processor 2 determines that the change of the system settings has not succeeded (NO in Step S226), it outputs a change failure notification to the information processing device 4 (Step S227). The control unit 21 of the information processing device 4 outputs a message including the fact that the change has failed to the display device 3 in response to the change failure notification output from the processor 2 (Step S430).

In a case in which the processor 2 determines that the change of the system settings has succeeded (YES in Step S226), it outputs a change success notification to the information processing device 4 (Step S228). The control unit 21 of the information processing device 4 outputs a message including the fact that the change has succeeded to the display device 3 in response to the change success notification output from the processor 2 (Step S431).

According to this embodiment, the information processing device 4 monitors a system abnormality using the learning model. Therefore, the processor 2 does not perform various processes, such as calculation or determination, and it is possible to reduce the load on the processor 2.

Embodiment 4

Figure 16:
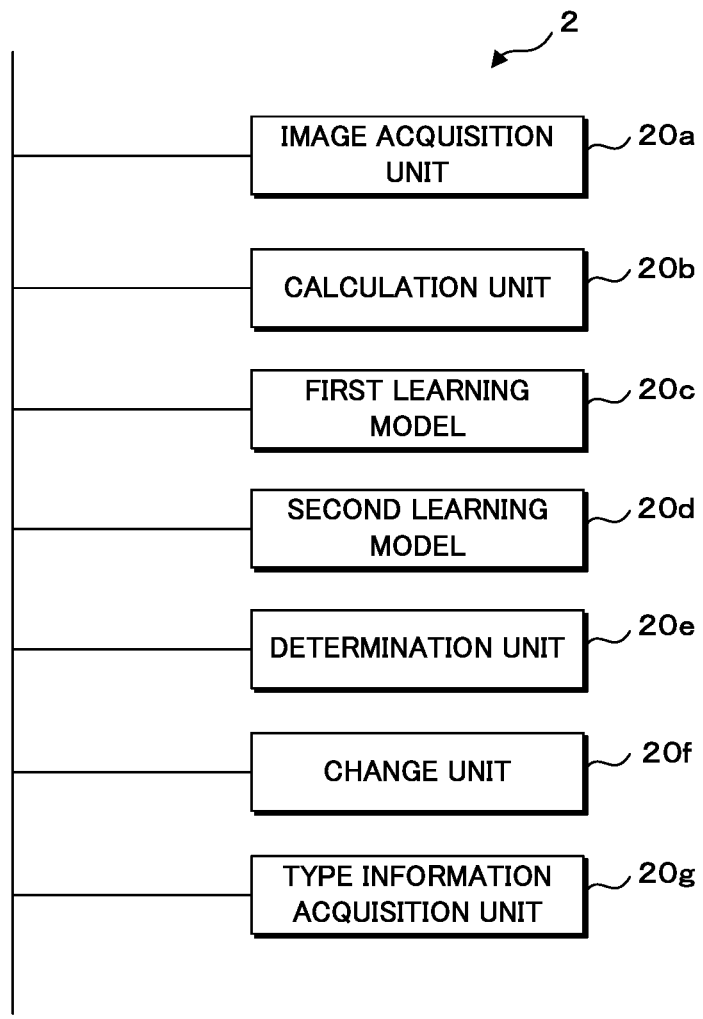
FIG. 16 is a functional block diagram illustrating the operation of the processor according to Embodiments 1 and 2.

FIG. 16 is a functional block diagram illustrating the operation of the processor 2 according to Embodiments 1 and 2. The control unit 21 executes the control program 2P such that the processor 2 operates as follows. In addition, the functional block diagram illustrating the operation is similarly applied to the information processing device 4 according to Embodiment 3.

An image acquisition unit 20a acquires the endoscopic image captured using the first system information. A calculation unit 20*b* calculates parameter on the basis of the endoscopic image acquired by the image acquisition unit 20*a*. A first learning model 20*c* outputs the discrimination result of discriminating the part of the subject in a case in which the parameter calculated by the calculation unit 20*b* is input.

A second learning model 20*d* outputs the second system information in a case in which the parameter calculated by the calculation unit 20*b* and the discrimination result output by the first learning model 20*c* are input. A determination unit 20*e* determines a difference between the second system information output by the second learning model 20*d* and the first system information. A change unit 20*f* changes the system settings on the basis of the determination result of the determination unit 20*e*. A type information acquisition unit 20*g* acquires the type information of the endoscope.

Embodiment 4 is as described above, and the other configurations are the same as those of Embodiments 1 to 3. Therefore, the corresponding portions are denoted by the same reference numerals, and the detailed description thereof will not be repeated.

It is to be noted that, as used herein and in the appended claims, the singular forms "a", "an", and "the" include plural referents unless the context clearly dictates otherwise.

It is to be noted that the disclosed embodiment is illustrative and not restrictive in all aspects. The scope of the present invention is defined by the appended claims rather than by the description preceding them, and all changes that fall within metes and bounds of the claims, or equivalence of such metes and bounds thereof are therefore intended to be embraced by the claims.

The invention claimed is:

1. A processor for an endoscope comprising:
a controller executing program code to perform operations of:
acquiring, by the controller, an endoscopic image captured using first system information including a value of an intensity of one of three color tones of light emitted by a light source of the endoscope, a value of an aperture of the light source, or a value of a voltage or a current provided to the light source;
calculating, by the controller, a parameter on the basis of the endoscopic image acquired by the controller;
discriminating a part of a subject using a first learning model that outputs a discrimination result of discriminating the part of the subject in a case in which the calculated parameter is input;
outputting second system information including the value of the intensity of one of three color tones of light emitted by the light source of the endoscope, the value of the aperture of the light source, or the value of the voltage or the current provided to the light source using a second learning model that outputs the second system information in a case in which the parameter and the discriminated part of the subject are input; and
determining, by the controller, a difference between the second system information output by the second learning model and the first system information.

2. The processor for an endoscope according to claim 1, further comprising:
changing, by the controller, system settings on the basis of a determination result determined by the controller.

3. The processor for an endoscope according to claim 2, wherein, in a case in which the controller has failed to change the system settings, the controller outputs a message including a change failure.

4. The processor for an endoscope according to claim 1, further comprising:
acquiring, by the controller, type information of an endoscope,
wherein the first learning model outputs the discrimination result of discriminating a part of a subject in a case in which the type information acquired by the controller and the parameter calculated by the controller are input.

5. The processor for an endoscope according to claim 4, wherein the second learning model outputs the second system information in a case in which the type information acquired by the controller, the parameter calculated by the controller, and the discrimination result output by the first learning model are input.

6. The processor for an endoscope according to claim 1, wherein the parameter include an average value of R, G, or B pixels values of pixels constituting the endoscopic image.

7. The processor for an endoscope according to claim 1, wherein
the first system information includes a value of an intensity of one of three color tones of a light source of the endoscope, a value of an aperture of the light source, and a value of a voltage or a current provided to the light source, and
the second system information includes the value of an intensity of one of three color tones of the light source of the endoscope, the value of the aperture of the light source, and the value of the voltage or the current provided to the light source.

8. The processor for an endoscope according to claim 1, wherein the parameter calculated by the controller includes a color tone parameter of the endoscope image, a brightness parameter of the endoscope image, a spatial frequency parameter of the endoscope image, or an image noise parameter of the endoscopic image.

9. The processor for an endoscope according to claim 1, wherein the parameter calculated by the controller includes a color tone parameter of the endoscope image, a brightness parameter of the endoscope image, a spatial frequency parameter of the endoscope image, and an image noise parameter of the endoscopic image.

10. The processor for an endoscope according to claim 1, wherein the parameter calculated by the controller includes
a color tone parameter of the endoscope image, the color tone parameter being
an average of R, G, or B pixel values of pixels of the entire endoscopic image or a predetermined range of the endoscope image, or
a frequency of appearance of the pixel values based on a histogram indicating an overall distribution of the pixel values in the endoscope image,
a brightness parameter of the endoscope image, the brightness parameter being
the brightness of each of R, G, and B pixels divided by three, or
the number of pixels corresponding to each brightness value based on a brightness histogram indicating the brightness distribution of the pixels in the endoscope image and the degree of bias of the distribution,
a spatial frequency parameter of the endoscope image, the spatial frequency parameter being a Fourier transform frequency distribution of image data of the endoscope image indicating the number of repetitions of a pattern included in a unit length, or an image noise parameter of the endoscopic image being a standard deviation defined by a square root of a variance of image data representing the endoscope image.

11. An endoscope system comprising:
a processor for an endoscope; and
an endoscope that is connected to the processor for an endoscope,
wherein the processor for an endoscope includes a controller executing program code to perform operation of:
acquiring, by the controller, an endoscopic image captured using first system information including a value of an intensity of one of three color tones of light emitted by a light source of the endoscope, a value of an aperture of the light source, or a value of a voltage or a current provided to the light source;
calculating, by the controller, parameter on the basis of the endoscopic image acquired by the controller;
discriminating a part of a subject using a first learning model that outputs a discrimination result of discriminating the part of the subject in a case in which the calculated parameter is input;
outputting second system information including the value of the intensity of one of three color tones of light emitted by the light source of the endoscope, the value of the aperture of the light source, or the value of the voltage or the current provided to the light source using a second learning model that outputs the second system information in a case in which the parameter and the discriminated part of the subject are input; and
determining, by the controller, a difference between the second system information output by the second learning model and the first system information.

12. The endoscope system according to claim 11, further comprising:
a light source emitting light of different colors and having an adjustable aperture; and
a current or voltage circuit configured to adjust the current or voltage applied to the light source.

13. The endoscope system according to claim 12, wherein the first system information includes a value of an intensity of one of three color tones of a light source of the endoscope, a value of an aperture of the light source, and a value of a voltage or a current provided to the light source, and
the second system information includes the value of an intensity of one of three color tones of the light source of the endoscope, the value of the aperture of the light source, and the value of the voltage or the current provided to the light source.

14. An information processing apparatus comprising one or a plurality of processors, the one or the plurality of processors executing the following operations of:
acquiring an endoscopic image captured using first system information including a value of an intensity of one of three color tones of light emitted by a light source of the endoscope, a value of an aperture of the light source, or a value of a voltage or a current provided to the light source;
calculating parameter on the basis of the endoscopic image acquired by the processor;
discriminating a part of a subject using a first learning model that outputs a discrimination result of discriminating the part of the subject in a case in which the calculated parameter is input;
outputting second system information including the value of the intensity of one of three color tones of light emitted by the light source of the endoscope, the value of the aperture of the light source, or the value of the voltage or the current provided to the light source using a second learning model that outputs the second system information in a case in which the parameter and the discriminated part of the subject are input; and
determining a difference between the second system information output by the second learning model and the first system information.

15. A non-transitory computer-readable storage medium storing a program that causes a computer to perform a process comprising operations of:
acquiring an endoscopic image captured using first system information including a value of an intensity of one of three color tones of light emitted by a light source of the endoscope, a value of an aperture of the light source, or a value of a voltage or a current provided to the light source;
calculating parameter on the basis of the acquired endoscopic image;
discriminating a part of a subject using a first learning model that outputs a discrimination result of discriminating the part of the subject in a case in which the calculated parameter is input;
outputting second system information including the value of the intensity of one of three color tones of light emitted by the light source of the endoscope, the value of the aperture of the light source, or the value of the voltage or the current provided to the light source using a second learning model that outputs the second system information in a case in which the parameter and the discriminated part of the subject are input; and
determining a difference between the output second system information and the first system information.

16. An information processing method comprising:
acquiring an endoscopic image captured using first system information including a value of an intensity of one of three color tones of light emitted by a light source of the endoscope, a value of an aperture of the light source, or a value of a voltage or a current provided to the light source;
calculating parameter on the basis of the acquired endoscopic image;
discriminating a part of a subject using a first learning model that outputs a discrimination result of discriminating the part of the subject in a case in which the calculated parameter is input;
outputting second system information including the value of the intensity of one of three color tones of light emitted by the light source of the endoscope, the value of the aperture of the light source, or the value of the voltage or the current provided to the light source using a second learning model that outputs the second system information in a case in which the parameter and the discriminated part of the subject are input; and
determining a difference between the output second system information and the first system information.

* * * * *